| 
US012098163B2

(12) United States Patent
Kim et al.

(10) Patent No.: US 12,098,163 B2
(45) Date of Patent: *Sep. 24, 2024

(54) METHOD FOR PRODUCING FUNCTIONAL CRYSTALLINE SWEETENER

(71) Applicant: SAMYANG CORPORATION, Seoul (KR)

(72) Inventors: Go-Eun Kim, Gwangju-si (KR); Jae-Kyung Yang, Hwaseong-si (KR); Kyung-Hun Ryu, Seongnam-si (KR); Sung Won Park, Yongin-si (KR); Ji Won Park, Suwon-si (KR); Eunsoo Cho, Seongnam-si (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/749,320

(22) Filed: May 20, 2022

(65) Prior Publication Data

US 2022/0315618 A1   Oct. 6, 2022

Related U.S. Application Data

(60) Division of application No. 16/968,650, filed as application No. PCT/KR2019/001536 on Feb. 7, 2019, now Pat. No. 11,401,292, which is a continuation of application No. PCT/KR2018/001829, filed on Feb. 12, 2018.

(30) Foreign Application Priority Data

Dec. 28, 2018   (KR) ........................ 10-2018-0172864

(51) Int. Cl.
*C07H 3/02*   (2006.01)

(52) U.S. Cl.
CPC ............ *C07H 3/02* (2013.01); *C07B 2200/13* (2013.01)

(58) Field of Classification Search
None
See application file for complete search history.

(56) References Cited

U.S. PATENT DOCUMENTS

2017/0313734 A1   11/2017   Kim et al.
2018/0049458 A1*   2/2018   Woodyer ................ A23L 33/15

FOREIGN PATENT DOCUMENTS

| CN | 106852145 | 6/2017 |
| CN | 107635412 | 1/2018 |
| KR | 10-2017-0072849 | 6/2017 |
| TW | 201619177 | 6/2016 |
| TW | 201639863 | 11/2016 |
| TW | 201904445 | 2/2019 |

OTHER PUBLICATIONS

Ye, Tielin et al., "Principle and application of chemical crystallization process," Beijing University of Technology Press, Apr. 30, 2006.

* cited by examiner

*Primary Examiner* — Layla D Berry
(74) *Attorney, Agent, or Firm* — LEX IP MEISTER, PLLC

(57) ABSTRACT

The present invention relates to a method for preparing a crystalline functional sweetener, and more specifically, relates to a method for preparing a crystalline functional sweetener for raising the crystallization yield and increasing the particle size by controlling the content of impurities or production of impurities comprised in a solution for preparing the crystal.

10 Claims, 6 Drawing Sheets

METHOD FOR PRODUCING FUNCTIONAL CRYSTALLINE SWEETENER

TECHNICAL FIELD

The present invention relates to a method for preparing a crystalline functional sweetener, and relates to a method for preparing an allulose crystal for raising the crystallization yield and increasing the particle size by controlling the content of impurities converted from allulose in the process of preparing the crystalline functional sweetener, for example, allulose crystal.

BACKGROUND ART

General saccharides represented by sugar and starch sugar form the biggest market of about 65 trillion won in the world, but as consumer's needs for health-oriented functional and premium products are strengthened around the world, the market of functional sweeteners such as sugar alcohols including xylitol, oligosaccharides including fructooligosaccharide, functional saccharides including crystalline fructose, and sweeteners including sucralose or aspartame, etc. has been grown.

The sweetener is the generic term for seasoning and food additives providing sweet taste. Sugar, glucose, fructose, etc. among numerous sweeteners are distributed the most widely as natural components, and are the most widely used for preparing processed food. However, as the negative aspects of sugar such as cavity, obesity, diabetes, etc. become more prominent, the alternative functional sweetener for sugar have been received attention worldwide.

Recently, there is an allulose as an alternative saccharide which can substitute for sugar or fructose as a functional sweetener. The allulose can be prepared by chemical or biological methods, but the processes of purification and concentration are required, since allulose is contained at a low amount of the product. However, as the concentrated syrup has a limited application, the need for crystalline powder is high. It is difficult to crystallize the allulose due to its low crystallinity.

Therefore, a method for preparing an allulose crystal for raising the crystallization yield and increasing the particle size by minimizing the content of impurities comprised in an allulose solution for crystallization or production of impurities in a preparation process of allulose, and controlling the content of impurities converted from allulose has been urgently needed.

DISCLOSURE

Technical Problem

The present invention relates to a method for preparing an allulose crystal for increasing the crystallization yield and the particle size by controlling the content of impurities or production of impurities contained in a solution for preparing a crystal.

In addition, the present invention is to provide a preparation method of allulose crystal which can produce an allulose having uniform particle size by properly controlling the crystal particle growth, thereby reducing the loss in the recovery process and increasing the crystallization yield for the higher productivity.

In addition, the present invention is to provide a composition for crystallizing an allulose in which the content of allulose conversion material (Impurity-S) is controlled in a specific range of content, thereby increasing the crystallization yield with uniform particle size and reducing the loss in the recovery process.

Technical Solution

The present invention relates to a composition for crystallization of allulose for providing uniform particle size and enhancing the crystallization yield by reducing the loss in the recovery process, in which the content of allulose conversion material (Impurity-S) is controlled at the specific content range, and a method for preparing an allulose crystal using the same. In addition, the present invention relates to a method for preparing an allulose crystal for raising the crystallization yield and increasing the particle size by controlling the content of impurities or the production of impurities contained in the solution for preparing the crystal.

Since the allulose is more unstable, as pH is lower and the temperature is higher (FIG. 2, FIG. 3), the content of allulose is changed in the actual production process, particularly the concentration step. This problem lowered the purity of high-purity allulose, and thus, largely affected the crystallization step. It was confirmed that the content of allulose conversion material (Impurity) produced additionally become higher, as the content of allulose was decreased in this process actually, and this component largely affected the crystallization of allulose. The inventors found that when the content of Impurity-S in the various allulose conversion materials was contained, this might act as an inhibitor for the growth of allulose crystal particle, thereby largely affecting the particle size of crystal particle and crystallization yield.

Therefore, the present invention may prevent to reduce the particle size of allulose, and provide the allulose having uniform particle size for performing the allulose crystallization process, by controlling the content of impurities (Impurity-S) to be specific content or lower in the step before and after the concentration following the high purity separation process. In addition, the growth of the particle with uniform particle size may reduce the loss in the recovery process and enhance the crystallization yield, thereby increasing the productivity.

In the allulose syrup which is a raw material used for the allulose crystallization process, various allulose conversion materials which are impurities other than allulose produced in the process of preparing the allulose may be included. Or, the allulose conversion material may be produced in the allulose crystallization process. By regulating (controlling) the specific conversion material (hereinafter, Impurity-S) in the conversion material lower than specific amount, for example, 2 wt/wt % or lower, the shape, structure and size, crystal purity, crystal production rate, and crystallization yield of allulose crystal particle can be enhanced. The Impurity-S acts as an inhibitor preventing the growth of crystal particle of allulose, and thus reduces the crystallization yield. In the present invention, a method for increasing the particle size of allulose crystal and the yield can be increased by controlling the production process of allulose under the condition that allulose conversion material is not produced.

The allulose conversion material (Impurity-S) may be a material having 10 to 600 m/z, 10 to 550 m/z, 10 to 500 m/z, 10 to 450 m/z, 10 to 400 m/z, 20 to 600 m/z, 20 to 550 m/z, 20 to 500 m/z, 20 to 450 m/z, 20 to 400 m/z, 30 to 600 m/z, 30 to 550 m/z, 30 to 500 m/z, 30 to 450 m/z, 30 to 400 m/z, 40 to 600 m/z, 40 to 550 m/z, 40 to 500 m/z, 40 to 450 m/z, 40 to 400 m/z, 50 to 600 m/z, 50 to 550 m/z, 50 to 500 m/z, 50 to 450 m/z, or 50 to 400 m/z of the ratio of mass/quantity of electric charge measured by LC/MS analysis, or a material having the maximum peak at the elution time 31±2 min measured by HPLC analysis. The LC/MS analysis is to analyze a material obtained by separating the material having the maximum peak at the elution time 31±2 min time measured by HPLC analysis.

In addition, the allulose conversion material (Impurity-S) may be modified products of allulose, polymers of the modified product of allulose, or an intermediate substance produced or conversed during the degradation of allulose. The lower limit of the molecular weight of the allulose conversion material (Impurity-S) may be 0.2 times or more, 0.3 times or more, 0.4 times or more, 0.5 times or more, 0.6 times or more, 0.7 times or more, 0.8 times or more, 0.9 times or more, 1 time or more, 1.1 times or more, 1.2 times or more, 1.3 times or more, 1.4 times or more, 1.5 times or more, 1.6 times or more, 1.7 times or more, 1.8 times or more, 1.9 times or more, or twice or more than the molecular weight of allulose. The upper limit of the molecular weight of the allulose conversion material (Impurity-S) may be 10 times or less, 9 times or less, 8 times or less, 7 times or less, 6 times or less, 5 times or less, 4 times or less, 3 times or less, 2 times or less, lower than 1.5 times, 1.5 times or less, 1.4 times or less, 1.3 times or less, 1.2 times or less, 1.1 times or less, 1 time or less, 0.9 times or less, 0.8 times or less, 0.7 times or less, 0.6 times or less, 0.5 times or less, 0.4 times or less, 0.3 times or less, or 0.2 times or less than the molecular weight of allulose. The allulose conversion material (Impurity-S) may have a molecular weight in a range set by a combination of the lower limit and the upper limit value. For example, the molecular weight of the allulose conversion material (Impurity-S) may modified products of allulose, polymer of modified product of allulose, or an intermediate substance produced or conversed during the degradation of allulose having a molecular weight of 0.4 times or more to 10 times, 0.5 times or more to 10 times, 0.53 times or more to 10 times, 0.4 times or more to 9 times, 0.5 times or more to 9 times, 0.53 times or more to 9 times, 0.4 times or more to 8 times, 0.5 times or more to 8 times, 0.53 times or more to 8 times, 0.4 times or more to 7 times, 0.4 times or more to 6 times, 0.4 times or more to 5 times, 0.4 times or more to 4 times, 0.4 times or more to 3 times, 0.4 times or more to 2 times, 0.4 times or more to less than 1.5 times, 0.4 times or more to 1.5 times or less, 0.4 times or more to 1.4 times, 0.4 times or more to 1.3 times, 0.4 times or more to 1.2 times, 0.4 times or more to 1.1 times, 0.4 times or more to 1 time, 0.4 times or more to 0.9 times, 0.4 times or more to 0.8 times, 0.4 times or more to 0.7 times, 0.4 times or more to 0.6 times, 0.4 times or more to 0.5 times, 0.5 times or more to 7 times, 0.53 times or more to 7 times, 0.4 times or more to 6 times, 0.5 times or more to 6 times, 0.5 times or more to 5 times, 0.5 times or more to 4 times, 0.5 times or more to 3 times, 0.5 times or more to 2 times, 0.5 times or more to less than 1.5 times, 0.5 times or more to 1.5 times or less, 0.5 times or more to 1.4 times, 0.5 times or more to 1.3 times, 0.5 times or more to 1.2 times, 0.5 times or more to 1.1 times, 0.5 times or more to 1 times, 0.5 times or more to 0.9 times, 0.5 times or more to 0.8 times, 0.5 times or more to 0.7 times, 0.5 times or more to 0.6 times, 0.53 times or more to 6 times, 0.4 times or more to 5 times, 0.5 times or more to 5 times, 0.53 times or more to 5 times, 0.4 times or more to 4 times, 0.5 times or more to 4 times, 0.53 times or more to 4 times, 1.5 times or more to 10 times, 2 times or more to 10 times, 2 times or more to 4 times of the molecular weight of allulose, and preferably, 0.4 times or more to 4 times of the molecular weight of allulose.

In an embodiment, as the allulose conversion material (Impurity-S) is continuously exposed by external stress, for example, high temperature or acidic condition, allulose denatured polymer as the allulose conversion material (Impurity-S) may be converted into the allulose denatured polymer (tetramer analogue of allulose) having the molecular weight similar to dimer. This is because the allulose is easily denatured by external stress and thus, the dehydration and condensation reactions are randomly repeated with allulose or allulose conversion material, resulting from the mechanism that it is converted into the denatured polymer. Alternatively, the allulose conversion material (Impurity-S) may be an intermediate substance produced or conversed during the degradation of allulose.

Specifically, the component detected in the molecular weight of 341 m/z is the component with increased content, as the raw material of crystallization containing allulose is treated severely and the material of dimer-like structure of allulose denatured by dehydration or condensation reaction. As the result of inferring the structure by LC-MS analysis, it can be predicted that the material has the chemical formula of C12H22O11, and is the allulose denatured polymer. It was confirmed that the content of allulose denatured polymers (tetramer analogues of allulose) having the molecular weight similar to dimer of allulose denatured polymer of C25H28O11, C24H42O21 or C24H44O22 was increased together with the material of dimer-like structure of allulose, as the thermal treatment was proceeded. This could be considered that the allulose was easily denatured by external stress, for example, thermal treatment, the dehydration and condensation reactions were randomly repeated with allulose or allulose conversion material, thereby being converted into the materials.

Specifically, as a result of an LC-MS analysis, the detected components in the allulose conversion material (Impurity-S) may contain an intermediate material (Furan aldehyde intermediate) produced during the decomposition of hexose such as allulose to HMF by dehydration reaction, $[C_6H_{12}O_6+Na]^+$ in which the Na+ion is bonded to the allulose, or $[C_6H_{12}O_6+Na]^+$ in which the Na+ion is bonded to the allulose dimer molecule.

In addition, as a result of inferring the chemical structure through LC-MS analysis, the allulose conversion material may contain a compound of molecular formula CxHyOz, wherein x may be an integer from 3 to 15, 3 to 14, 3 to 13, 3 to 12, 4 to 15, 4 to 14, 4 to 13, 4 to 12, 5 to 15, 5 to 14, 5 to 13, or 5 to 12, y may be an integer from 1 to 15, 1 to 14, 1 to 13, 1 to 12, 2 to 15, 2 to 14, 2 to 13, 2 to 12, 3 to 15, 3 to 13, 3 to 12, 4 to 15, 4 to 14, 4 to 13, or 4 to 12, and z may be an integer from 1 to 10, 1 to 9, 1 to 8, 1 to 7, or 1 to 6.

For example, the allulose conversion material may contain a compound having molecular formula of $C_5H_4O_3$, $C_5H_6O_4$, $C_5H_8O_3$, $C_5H_4O_2$, $C_5H_{10}O_3$, $C_6H_4O_5$, $C_6H_{10}O_3$, $C_6H_4O_4$, $C_6H_6O_3$, $C_6H_8O$, $C_6H_4O_5$, $C_6H_6O_4$, $C_6H_4O_4$, $C_6H_4O_3$, $C_6H_8O_3$, $C_{11}H_8O_6$, $C_{12}H_{12}O_5$, or $C_{12}H_{10}O_5$.

Specifically, the allulose conversion material may contain one or more kinds of compounds selected from the group consisting of levulinic acid (4-oxopentanoic), furfural, Hydroxymethylfurfural (HMF), γ-Hydroxyvaleric acid (GVB), 2,5-Dimethylfuran, 2,5-furandicarboxylic acid (FDCA), 5-hydroxymethyl-2-furoic acid, 2,5-formylfurancarboxylic acid, 2,5-Furandicarbaldehyde, 2,5-bis-(hydroxymethyl)furan, bis(5-formyl-2-furfuryl) ether, 2-Furoic acid, 3-Furoic acid, 5-Hydroxyfurfural, 2,5-Dihydro-2,5-dimethoxyfuran, (2R)-5-Oxotetrahydro-2-furancarboxylic acid, 2,5-formylfuran carboxylic acid, 5,5'-Methylenedi(2-furoic acid), and bis(5-methyl furfuryl) ether.

According to the present invention, it is to provide a method for removing or reducing the content of conversion material (Impurity-S) contained in the allulose syrup that is a raw material used for the allulose crystallization process, by performing the production, separation and/or purification process of allulose under the condition that the allulose conversion material is not produced. Accordingly, the crystal shape and crystallization yield can be enhanced by reducing the content of Impurity-S in the raw material of crystallization and lowering the content of impurities which prevents the crystal growth.

Specifically, the content of conversion material (Impurity-S) may be controlled by a method for preventing or reducing the production of Impurity-S, or removing or reducing the produced Impurity-S. In one embodiment of the present invention, as the method for controlling the production process of allulose under the condition that the production of allulose conversion material is inhibited or reduced, the allulose crystal particle size may be increased and the crystal can be formed in the shape close to quadrate, and the allulose yield can be enhanced. More specifically, the allulose crystal particle growth and yield can be enhanced, when the content of allulose conversion material (Impurity-S) component in the crystallization undiluted solution as 2 wt/wt % or lower.

The method for inhibiting or reducing the production of Impurity-S may be achieved by controlling the condition that the allulose conversion material is not produced, particularly the condition of production process of allulose such as control of pH, temperature, conductivity particularly in the concentration process. In addition, the method for removing or reducing the produced Impurity-S may use a method for performing an activated carbon treatment or a method of secondary crystallization by re-dissolving the crystal obtained in the primary crystallization, etc., and a method for removing impurities in the allulose syrup may be used.

Specifically, the method of controlling the production or content of impurities may be conducted with one or more methods among the following methods.

As one embodiment, one embodiment of the method for inhibiting or reducing the production of allulose conversion material (Impurity-S) in the allulose production process may be a method for performing the allulose production process under pH 4 or higher and/or 70° C. or lower temperature. Specifically, since it is relatively stable under the condition of pH 4 to 7 or pH 4 to 6 and the temperature of 70° C. or lower, preferably 60° C. or less, it is preferable to consistently manage it not to be exposed by external stress, by managing the temperature of reaction solution not to be over 70° C., preferably over 60° C., in the allulose production process like decoloring, ion purification, high purity separation, etc., and particularly performing the concentration process as divided into 2 steps or more.

To inhibit or reduce the production of Impurity-S in the allulose production process may be performed for the allulose fraction obtained in SMB chromatography separation process under the temperature condition of 40 to 70° C. or lower, and selectively, the concentration process may be conducted as divided into at least 2 steps or more. For example, when the concentration process is conducted as divided into 2 steps, the allulose syrup may be concentrated to be 30~50 Bx concentration, and the primary concentrate may be secondarily concentrated to be 60~85 Bx concentration again, and preferably an activated carbon treating process may be further comprised between the primary concentration process and the secondary concentration process, thereby removing the Impurity-S comprised in concentrates or reducing the content.

In another embodiment, the method for removing or reducing the content of conversion material (Impurity-S) comprised in the allulose syrup which is a raw material for allulose crystallization is to act as impurities by treating an activated carbon, or to remove it by adsorbing high molecular or small molecular organic matter, colored ionic material or protein, etc., which can induce the denaturation of allulose.

In detail, the content of conversion material (Impurity-S) may be removed or reduced by performing a process of treating an activated carbon before concentrating the allulose fraction obtained by conducting SMB chromatography separation process for the allulose reaction solution obtained from a substrate. The activated carbon process may be performed additionally, after performing an ion purification process of allulose fraction obtained in SMB chromatography separation process.

The activated carbon process may perform a solid-liquid separation process for the reaction solution comprising the activated carbon after contacting an activated carbon to the allulose solution and reacting them at the temperature of 40 to 50° C. for 0.5 to 5 hours, thereby collecting a remainder, and the impurities may be removed as filtration residues. The filtration may be carried out by using a filtration equipment like a filter press.

In the activated carbon reaction process, stirring may be carried out selectively, and the stirring rate of reaction solution may be 5 to 500 rpm, preferably 50 to 300 rpm. The stirring rate may be properly selected in consideration of dispersion degree of activated carbon and expense cost for stirring. The contacting time of activated carbon and reaction solution may be properly selected in consideration of dispersion degree of activated carbon and efficiency of removal of impurities, etc., and for example, may be 0.5 to 5 hours, preferably 0.5 to 2 hours, and when the contacting time is short, the removal of impurities, for example, decoloring may be not sufficiently achieved, and when the contacting time is long, destruction and browning of major components may be caused.

The activated carbon used for the activated carbon treatment process may be derived from Carboniferous system or Lignocellulosic system, and may remove the impurities selectively according to the pore diameter size of activated carbon.

As additional one embodiment, the method for inhibiting or reducing the production of allulose conversion material (Impurity-S) of allulose crystallization composition is to carry out recrystallization. The content of allulose conversion material (Impurity-S) may be removed or reduced in the primary crystallization process, by inputting it into the secondary crystallization process, after conducting the primary crystallization of allulose solution passed through the high purity separation and concentration processes and dissolving the allulose crystal recovered by removing the supernatant in the primary crystallization undiluted solution for dehydration in water again.

Accordingly, one embodiment of the present invention provides a method for controlling the content of allulose conversion material (Impurity-S) comprised in the allulose composition for crystallization as 2 wt/wt % or less on the basis of content of solid of composition.

The method may be performed by controlling one or more kinds of conditions selected from the group consisting of pH condition and temperature condition, and the pH condition may be in the range of pH 4 to 7, or the temperature condition may be 70° C. or lower.

The allulose composition for crystallization may be prepared by treating the reaction solution containing allulose by SMB chromatography separation process and concentrating the obtained allulose solution at the temperature condition of 40 to 70° C. or lower. The concentration process may be performed as divided into at least 2 steps, and it may be performing the primary concentration of allulose solution to be 30~50 Bx concentration, and the secondary concentration of the primary concentrate to be 60~85 Bx concentration again. An activated carbon treating process may be further conducted before performing the concentration process.

Another embodiment of the present invention relates to a composition for crystallizing an allulose comprising the content of allulose conversion material (Impurity-S) of 2 wt/wt % or lower, 1.9 wt/wt % or lower, 1.8 wt/wt % or lower, 1.7 wt/wt % or lower, 1.6 wt/wt % or lower, 1.5 wt/wt % or lower, 1.4 wt/wt % or lower, 1.3 wt/wt % or lower, 1.2 wt/wt % or lower, 1.1 wt/wt % or lower, 1.0 wt/wt % or lower, 0.9 wt/wt % or lower, 0.8 wt/wt % or lower, 0.7 wt/wt % or lower, 0.65 wt/wt % or lower, 0.6 wt/wt % or lower, 0.5 wt/wt % or lower, 0.4 wt/wt % or lower, 0.3 wt/wt % or lower, 0.2 wt/wt % or lower, 0.1 wt/wt % or lower, preferably 1.0 wt/wt % or lower on the basis of total solid content of composition of 100 wt/wt %, and it is more preferable not to include impurities.

Preferably, the composition for crystallizing an allulose may comprise the content of allulose of 90 wt/wt % or more, 91 wt/wt % or more, 92 wt/wt % or more, 93 wt/wt % or more, 94 wt/wt % or more, or 95 wt/wt % or more, on the basis of total solid content of composition of 100 wt/wt %.

The viscosity of allulose composition for crystallization may be 2 cps to 200 cps at the temperature of composition of 45° C., and the conductivity may be 1,000 uS/cm or lower, for example 0.01 to 1,000 uS/cm, preferably 30 uS/cm or lower, for example 0.1 to 30 uS/cm. The conductivity of composition for crystallizing the allulose is preferable as lower. The conductivity of allulose syrup is the value measured on the basis of content of solid of 30 Bx.

The allulose solution for crystallization may have the content of solid of 60 or more to 85 Bx or less, for example higher than 60 Bx to 80 Bx, 65 to 85 Bx, 65 to 80 Bx, or 68 to 85 Bx.

One embodiment of the present invention relates to a method for preparing an allulose crystal by using the allulose solution for crystallization, and more specifically, a method for preparing an allulose crystal comprising a step of providing a composition for crystallizing an allulose comprising the content of allulose conversion material (Impurity-S) of 2 wt/wt % or less, 1.9 wt/wt % or less, 1.8 wt/wt % or less, 1.7 wt/wt % or less, 1.6 wt/wt % or less, 1.5 wt/wt % or less, 1.4 wt/wt % or less, 1.3 wt/wt % or less, 1.2 wt/wt % or less, 1.1 wt/wt % or less, 1.0 wt/wt % or less, 0.9 wt/wt % or less, 0.8 wt/wt % or less, 0.7 wt/wt % or less, 0.65 wt/wt % or less, 0.6 wt/wt % or less, 0.5 wt/wt % or less, 0.4 wt/wt % or less, 0.3 wt/wt % or less, 0.2 wt/wt % or less, 0.1 wt/wt % or less, preferably 1.0 wt/wt % or less on the basis of total content of solid of composition of 100 wt/wt %, and a step of preparing an allulose crystal by cooling the allulose aqueous solution.

In one specific embodiment of the present invention, the method for preparing the allulose crystal may comprise a step of secondary ion purification of allulose fraction obtained in SMB chromatography separation process, a step of concentrating the ion purified allulose fraction, and a step of obtaining an allulose crystal and allulose crystallization mother liquor by crystallizing an allulose from the concentrate, and selectively, may further comprise a recovery process, washing process and drying process of allulose crystal.

In addition, the content of allulose conversion material (Impurity-S) may be reduced or removed by treating the solution which the allulose fraction obtained in SMB chromatography separation process itself, or the solution of ion purifying the allulose fraction, before the concentration step, with an activated carbon. In addition, the content of allulose conversion material (Impurity-S) may be reduced or removed by performing the primary crystallization after concentrating the allulose solution for crystallization and performing the secondary crystallization by dissolving the obtained crystal.

In one specific embodiment of the present invention, the method for preparing the allulose crystal may comprise a step of the secondary ion purification of allulose fraction obtained by treating the allulose-containing reaction solution prepared from the substrate by SMB chromatography separation process and a step of concentrating the ion purified allulose fraction, or may comprise a process of ion purification treating the allulose fraction obtained by treating by SMB chromatography separation process, an activated carbon treating process, or both of activated carbon treating process and ion purification process.

The step of providing the allulose composition for crystallization relates to a method for preparing an allulose crystal, to comprise the content of allulose conversion material (Impurity-S) of 2 wt/wt % or less, 1.9 wt/wt % or less, 1.8 wt/wt % or less, 1.7 wt/wt % or less, 1.6 wt/wt % or less, 1.5 wt/wt % or less, 1.4 wt/wt % or less, 1.3 wt/wt % or less, 1.2 wt/wt % or less, 1.1 wt/wt % or less, 1.0 wt/wt % or less, 0.9 wt/wt % or less, 0.8 wt/wt % or less, 0.7 wt/wt % or less, 0.65 wt/wt % or less, 0.6 wt/wt % or less, 0.5 wt/wt % or less, 0.4 wt/wt % or less, 0.3 wt/wt % or less, 0.2 wt/wt % or less, 0.1 wt/wt % or less, preferably 1.0 wt/wt % or less, on the basis of total content of solid comprised in the composition for crystallization or not to comprise the allulose conversion material (Impurity-S).

The preparation method of allulose crystal according to the present invention may have the crystallization yield of allulose of 45% or more, preferably 48% or more, 50% or more, 53% or more, 54% or more, more preferably 55% or more, 56% or more, 57% or more, 58% or more, 59% or more, or 60% or more.

The controlling the content of allulose conversion material may be performed by controlling one or more kinds selected from the group consisting of pH condition and temperature of allulose solution, and the pH control may be achieved in pH 4 to 7 range, pH 4.5 to 7, or pH 5 to 7, preferably pH 5 to 7, and the temperature control may be achieved by controlling it in the range of 80° C. or lower, 75° C. or lower, 70° C. or lower, preferably 30 to 70° C. or lower, 30 to 69° C., 30 to 65° C. or 30 to 60° C.

Since the allulose is unstable as pH is low and the temperature is high, the content of allulose is changed in the concentration step in the actual production process. This problem lowered the purity of high purity of allulose, and therefore, largely affected the crystallization step. It was confirmed that the content of specific allulose conversion material (Impurity) produced additionally as the content of allulose was decreased in this process actually, and this component largely affected the crystallization of allulose. It was confirmed that when the content of component of Impurity-S in the various allulose conversion materials was over 2%, this might act as major barrier factor for the growth of allulose crystal particle, and thereby largely affect the particle size of crystal particle and crystallization yield.

Figure 1:
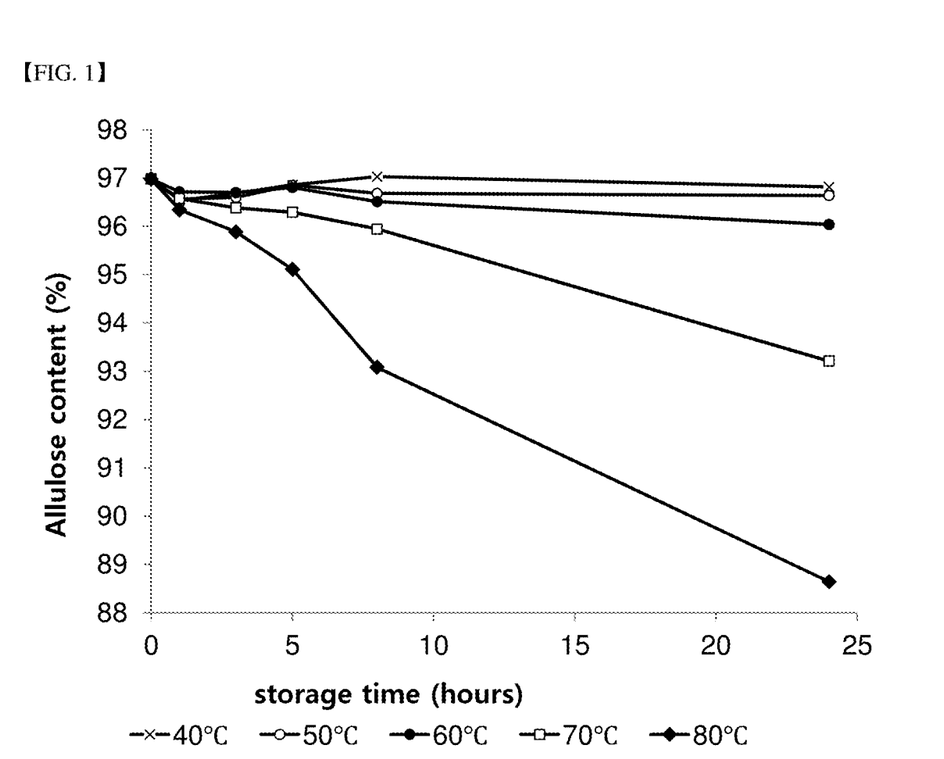
FIG. 1 is a graph showing the change of content of allulose, when the allulose syrup of pH 5 and 70 Brix concentration was stored by temperature.
Figure 2:
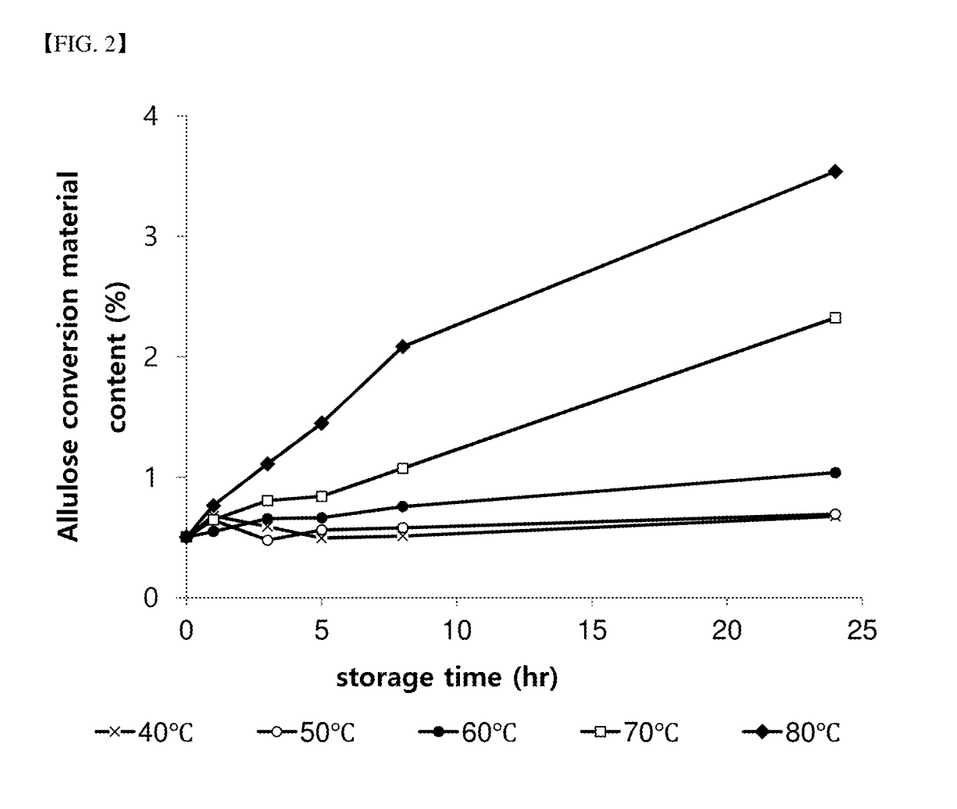
FIG. 2 is a graph showing the change of content of allulose conversion material, when the allulose syrup of pH 5 and 70 Brix concentration was stored by temperature.
Figure 3:
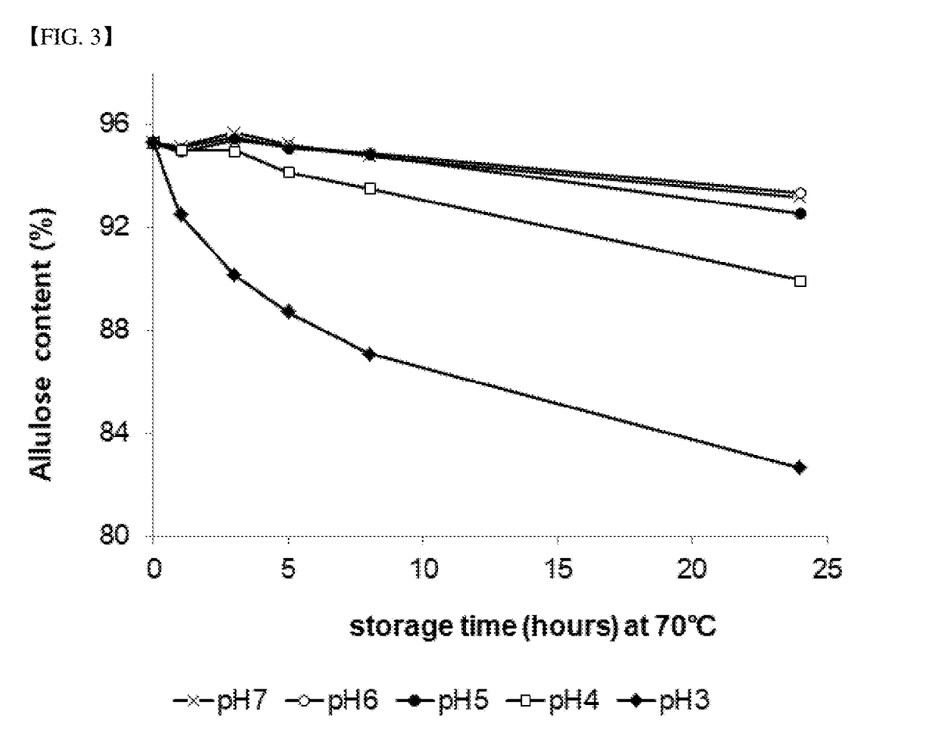
FIG. 3 is a graph showing the change of content of allulose, when the allulose syrup of different pH and 70 Brix concentration was stored at the temperature of 70° C.
Figure 4:
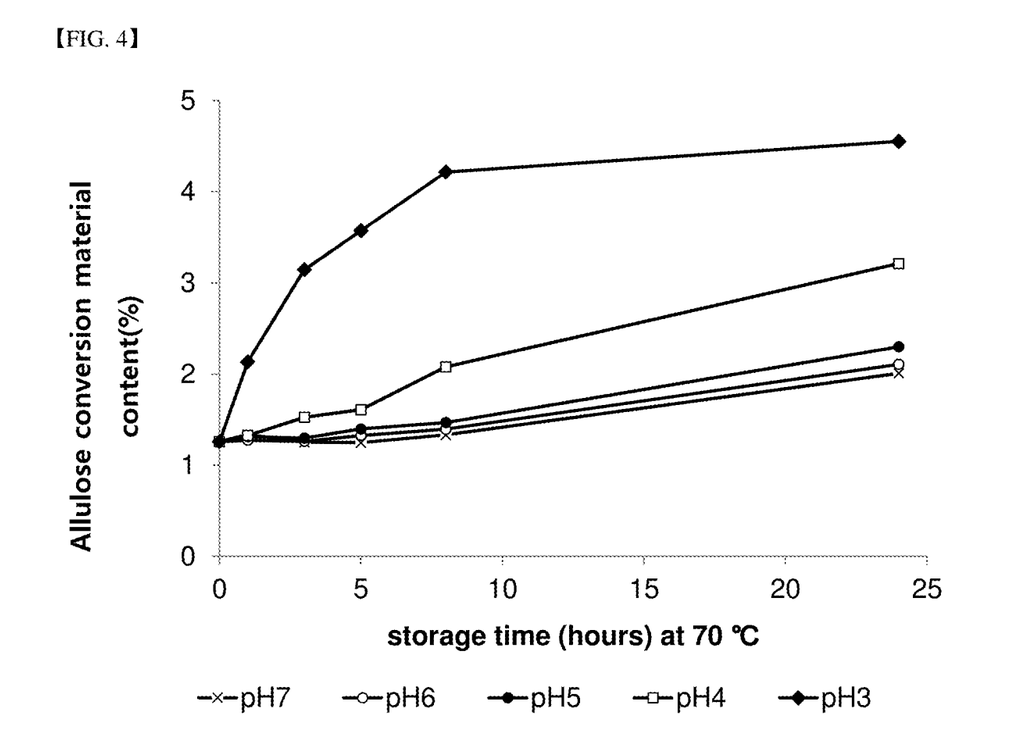
FIG. 4 is a graph showing the change of content of allulose conversion material, when the allulose syrup of different pH and 70 Brix concentration was stored at the temperature of 70° C.

Specifically, as shown in FIG. 1 and FIG. 2, as the storage temperature was higher, the content of allulose was decreased and the content of allulose conversion material (Impurity-S) was increased. As shown in FIG. 3 and FIG. 4, as pH was lower at the temperature of 70° C., the content of allulose was decreased and the production of allulose conversion material was increased.

The allulose composition for crystallization according to the present invention may be a reactant containing the allulose obtained by a biological or chemical method, an allulose fraction obtained by isolating the reactant with SMB chromatography, or a concentrate concentrating the allulose fraction. Before conducting the concentration process for preparing the allulose concentrate, ion purification and/or activated carbon treating process may be further performed, and the concentration process may be performed divided into at least 2 steps. The reactant containing the allulose may be obtained from a fructose substrate by a biological or chemical method, and preferably may be prepared by using an allulose converting enzyme or a microorganism producing the enzyme as the biological method.

For the allulose reaction solution, a separation process of allulose conversion reactant comprising ion purification and simulated moving bed (SMB) chromatograph separation process. In specific one embodiment, the allulose conversion reactant is separated as allulose fraction having higher allulose content than the converted reactant and fructose raffinate by performing the ion purification and SMB chromatograph separation process, and the allulose fraction is input into the crystallization process through the allulose concentration process.

The content of allulose in the allulose solution to collect the allulose crystal should be comprised at the high concentration as the supersaturated state, but as the content of allulose of allulose converted reactant was low, direct crystallization could not be conducted, and to increase the content of allulose before the crystallization step, the purification and concentration process by the desirable level should be carried out.

The method for obtaining the composition may perform the concentration process at the temperature of high purity allulose solution of 90° C. or less, 85° C. or less, 80° C. or less, 75° C. or less, 70° C. or less, lower than 70° C., for example, 40 to 70° C. or less, and specifically perform it by using a thin film evaporator or multiple effect evaporator. In one specific embodiment of the present invention, the step of concentrating the purified allulose solution may be performed at the temperature condition of 40 to 70° C. or less. When the temperature of concentrate is higher than 70° C., the thermal denaturation of D-allulose could be caused, and thus, the allulose conversion material (Impurity-S) according to the present invention may be produced or increased. In addition, since the temperature of reactant was rapidly increased by heat of vaporization as proceeding the concentration, it should be rapidly concentrated as maintaining the temperature of concentrate as 70° C. or less.

Specifically, the concentration process of allulose fraction obtained in the SMB chromatography separation process may be performed by various methods, and it may be carried out so as that the content of solid of concentrate is 70 Brix or more. For example, the allulose fraction obtained by the simulated moving bed separation method (for example, 20~30 wt % of solid content) may be concentrated by the solid content of 60 Brix or more by the concentration process. The composition for crystallizing the allulose according to the present invention may have the solid content of 60 to 85 Bx or less, for example, higher than 60 Bx to 85 Bx, 65 to 85 Bx, 70 to 85 Bx, 75 to 85 Bx, higher than 60 Bx to 83.5 Bx, 65 to 83.5 Bx, 70 to 83.5 Bx, or 75 to 83.5 Bx.

As one embodiment, the composition for crystallization may be an allulose fraction obtained by performing the simulated moving bed (SMB) chromatography separation process by using a column chromatograph filled with cation exchange resin in which calcium active group is attached, and specifically, may be an allulose fraction obtained by obtaining the allulose converted reactant which converted the fructose-containing raw material to allulose by using a biological catalyst and performing the activated carbon treating, ion purification and simulated moving bed (SMB) chromatography separation processes of allulose converted reactant. The allulose fraction may be obtained in the SMB chromatograph separation process itself or collected by passing through the ion purification process. The fructose content of fructose-containing raw material is 85 wt % or more on the basis of total content of solid of 100 wt %, and it may use a biological catalyst having the allulose conversion rate of allulose conversion reaction of 15% to 70%.

For the allulose fraction obtained in the SMB chromatography separation process, ion purification and/or activated carbon treatment process may be further conducted, before performing the concentration process.

The method for preparing the allulose crystal according to the present invention may control the temperature and concentration of solution of allulose concentrates to crystallizing it, and specifically, the supersaturated condition required for crystallization may be maintained by reducing the temperature of allulose solution or changing the concentration of D-allulose in the D-allulose solution. In one specific embodiment of the present invention, the crystallization progress may be monitored by observing the sample collected at a constant interval in the crystallization step with the naked eye or microscope, or analyzing the concentration of sugar in the supernatant collected by centrifugation of sample, and according to the result, the temperature or concentration of D-allulose may be controlled. For preparing the allulose crystal, when the solution of allulose concentrates are cooled and crystallized, the crystal growth may be induced by performing temperature rising and cooling repeatedly, after rapidly cooling in the temperature range of 10 to 25° C. through a heat exchanger.

The method for preparing the allulose crystal according to the present invention may control the temperature and concentration of solution of allulose concentrates to crystallizing it, and specifically, the supersaturated condition required for crystallization may be maintained by reducing the temperature of allulose solution or changing the concentration of D-allulose in the D-allulose solution. The method for preparing the allulose crystal according to the present invention may be performed by various methods, preferably by a cooling method. One embodiment of cooling method according to the present invention may produce a crystal by inducing a supersaturated state by cooling the allulose solution by the temperature range of 35 to 10° C. It is better to maintain the cooling rate as 0.01 to 20° C./min, and when the cooling rate is low, the time for forming a crystal is long and thus the productivity may be low, and when the cooling rate is high, a small particle size of crystal is formed, and thus the recovery of crystal may be difficult.

The preparation method of allulose crystal may comprise a step of producing a crystalline nucleus in an allulose solution comprising 90 wt/wt % or more allulose and having 60 to 85 Brix and 1,000 uS/cm or lower of conductivity, and a step of growing a crystal by lowering the temperature of the solution.

Specifically, the preparation method of allulose crystal may comprise a step of producing a crystalline nucleus by slowly stirring an allulose solution comprising 90 wt/wt % or more allulose and having 60 to 85 Brix at the temperature of 20 to 40° C., or 30 to 40° C., for example 35° C., and a step of growing a crystal by lowering the temperature of the solution. The method may be further comprise a step of redissolving microcrystals produced during cooling by increasing the temperature of solution in the range of 30 to 35° C., one or more times. The preparation method of allulose crystal may further comprise a process of adding a seed. The seed addition step and redissolving step may be comprised in the preparation method of allulose crystal respectively selectively, or both steps may be comprised.

Generally, it is known that the bigger the size of allulose crystal is, the better the properties are and the more the use convenience is increased, and for preparing the big size of crystal, a seed crystal classified by a transferring process and a main crystallization process should be performed all, but the crystallization process according to the present invention can easily prepare a relatively big sized of crystal with high yield by only one step process.

In addition, the crystallization process may perform a process of dissolving a microcrystal by increasing the temperature range of 30 to 35° C. of solution to redissolve the microcrystal formed in the cooling of the crystal growing process. In the crystallization process according to the present invention, the crystal growing process and microcrystal dissolving process may be repeated and carried out one or more times.

In the process for preparing the crystal, a seed may be further added in a purpose of increasing the crystal producing rate and size.

In specific one embodiment according to the present invention, the allulose crystal may be prepared by growing the crystal by cooling the temperature by 10° C. as decreasing the temperature by 1° C. per hour, after producing a small amount of crystal nucleus by stirring at the temperature of 35° C. an allulose solution which comprises 90 wt/wt % or more of allulose and has 60 to 85 Brix of total solid content, and optionally, by further including a step of dissolving the microcrystal by increasing the temperature of solution by 30 to 35° C. for redissolving the microcrystal produced during the cooling at least one or more time, to prepare the allulose crystal.

The method for preparing the allulose crystal according to the present invention may further comprise a step of recovering the allulose crystal collected in the crystallization step with various solid-liquid separation methods, for example, centrifugation, a step of washing with deionized water, and a step of drying. The drying step may be performed in a fluidized bed drier or vacuum drier, but not limited thereto.

An allulose crystal can be prepared by the method of cooling the allulose composition for crystallization according to the present invention. The allulose composition for crystallization is same as aforementioned.

The allulose comprised in the allulose crystal may be 94 wt/wt % or more, 95 wt/wt % or more, 96 wt/wt % or more, 97 wt/wt % or more, 98 wt/wt % or more, or 99 wt/wt % or more, based on 100 wt/wt % of total solid content.

Herein, "purity of crystal" means the purity of allulose crystal. The properties including the purity of crystal of the present invention may be obtained by methods such as for example, X-ray powder diffraction analysis, differential scanning calorimetry (DSC) analysis, infrared spectroscopic (FTIR) analysis, HPLC analysis, LC/MS analysis, etc., and the purity may be specifically analyzed by HPLC chromatography.

The allulose crystal according to one embodiment of the present invention may be an allulose crystal having an X-ray spectroscopy which has a peak at angles of diffraction (2θ) of 15.24, 18.78, and 30.84±0.2° in the X-ray spectroscopy. In one embodiment of the present invention, the X-ray spectroscopy may be the an allulose crystal having an X-ray spectroscopy which has a peak at angles of diffraction (2θ) of 15.24, 18.78, 30.84 and 28.37±0.2°, angles of diffraction (2θ) of 15.24, 18.78, 30.84 and 31.87±0.2°, or angles of diffraction (2θ) of 15.24, 18.78, 30.84 and 47.06. The angles of diffraction having the peak in the X-ray spectroscopy of the allulose crystal are the result of X-ray diffraction analysis by selecting and representing the upper (Relative Intensity %) major peaks and morphology specific peaks.

The allulose crystal according to the present invention may be obtained by various crystallization methods, but the characteristics may be measured with allulose crystals prepared by a cooling method.

The allulose crystal according to the present invention may have the Tm temperature of 125.8° C.±5° C. or enthalpy of melting (ΔH) of 200 to 220 J/g, according to DSC analysis, and the Tm may be 125.8° C.±3° C. The differential scanning calorimetry analysis (DSC) is operated according to the temperature gradient, and it measures the energy provided to maintain the temperature increase of allulose powder sample. It could be predicted that the higher the thermal capacity is in the DSC analysis of crystal, the more difficult it is easily dissolved, and the higher the thermal capacity and the more narrow the width of endothermic peak are, the crystal is formed more homogeneous and the harder.

Another embodiment of the present invention is an allulose crystal prepared with the composition for allulose crystallization, and may be an allulose having one or more kinds of characteristics selected from the group consisting of the following (1) to (5):

(1) an X-ray spectroscopy which has a peak at angles of diffraction (2θ) of 15.24, 18.78, and 30.84±0.2° in the X-ray spectroscopy, (2) a Tm temperature of 125.8° C.±5° C. according to a differential scanning calorimetry analysis (DSC), (3) an enthalpy of melting (ΔH) of 200 to 220 J/g according to a differential scanning calorimetry analysis, (4) a mean long diameter of 350 μm or more, preferably 350 to 2,000 μm, and (5) a ratio of long diameter length (micrometer) to short diameter of the crystal (=long diameter/short diameter) in the range of 1.0 to 8.0.

The allulose crystal according to the present invention, the mean short diameter (minor diameter) of crystal may be 50 to 1,000 μm, preferably 50 to 500 μm, and the mean long diameter (major diameter) may be 350 μm or more, preferably 350 to 2,000 μm, more preferably 400 μm or more to 2,000 μm.

In addition, the ratio of long diameter length (micrometer) to short diameter of the crystal (=long diameter/short diameter) of allulose crystal according to the present invention may be 1.0 to 8.0, 1.0 to 6.9, 1.0 to 6.0, 1.0 to 5.5, 1.0 to 5.0, 1.1 to 8.0, 1.1 to 6.9, 1.1 to 6.0, 1.1 to 5.5, 1.1 to 5.0, 1.3 to 8.0, 1.3 to 6.9, 1.3 to 6.0, 1.3 to 5.5, 1.3 to 5.0, 1.5 to 8.0, 1.1 to 6.9, 1.5 to 6.0, 1.5 to 5.5, 1.5 to 5.0, 2.0 to 8.0, 2.0 to 6.9, 2.0 to 6.0, 2.0 to 5.5, 2.0 to 5.0.

By the result of XRD pattern analysis of powder of allulose crystal according to the present invention, the allulose crystal according to the present invention is a pure crystal particle, and has a structure of rectangle hexahedron or close thereto. It is more preferable, since the uniformity and solidity of crystal is increased, as the crystal structure of the present invention closes to a cubic system.

In addition, as the crystal prepared in the crystallization process of allulose is homogeneous, the strength of crystal is increased and particle breakage is minimized, and thereby the particle-size distribution becomes homogeneous, and therefore the flowability may be enhanced. On the other hand, when the uniformity is low, it may be micronized by breakage of crystal particles at the drying and transferring stages, and may be relatively easily dissolved, and thus it affects the quality of product negatively.

The allulose crystal of the present invention has better flowability than micronized powder, and is stable during storage because it is not likely to be caked, and has the characteristic in that distribution and treatment are easy. In addition, the allulose powder has lower calories than sugar, and the sweetness is similar to sugar, and thus it may be used for easily and advantageously carry out the preparation of mixed sweeteners, solid mixed sweeteners, chocolate, chewing gum, instant juice, instant soup, granules, tablets, etc. Furthermore, the allulose crystal powder may be used by comprised in various kinds of compositions such as food and beverages, favorite dainty, feed, cosmetics, drugs, etc.

Effect of the Invention

The method for preparing an allulose crystal according to the present invention can prevent reducing the particle size of allulose by controlling the content of allulose conversion material (Impurity-S) content comprised in a solution for preparing the crystal and can produce an allulose having uniform particle size by properly controlling the crystal particle growth. In addition, by growing the particle as homogeneous size, the loss in the recovery process can be reduced and the crystallization yield can be enhanced, thereby increasing the productivity.

DETAILED DESCRIPTION OF THE EMBODIMENTS

The present invention will be described in more detail by the following examples. However, the following examples are desirable examples of the present invention, and the present invention is not limited thereto.

Example 1: Allulose Crystal Preparation

The allulose syrup was prepared from the fructose substrate with the substantially same biological method as the preparation method disclosed in Korean laid-open patent application no. 2014-0054997. After desalting the allulose syrup by passing through the column at the room temperature filled with the cation exchange resin, anion exchange resin and resin mixed of cation and anion exchange resins at the rate of 2 times (1-2 times) ion exchange resin volume per hour to remove impurities like colored and ion components, etc., the high purity of allulose solution was separately collected by using the chromatography filled with the $Ca^{2+}$ type of ion exchange resin.

The high-purity syrup of allulose containing 97 wt/wt % of allulose with 35 Bx (w/w %) was obtained through the high purity separation process (SMB) and concentrated, thereby preparing the allulose syrup for crystallization containing 97 wt/wt % of allulose with 81 Bx (w/w %) and the conductivity of 12 uS/cm. The conductivity of allulose syrup was the value measured on the basis of the solid content of 30 Bx.

The concentrated allulose syrup for crystallization was cooled slowly from the temperature of 35° C. of the supersaturated state to the temperature of 10° C., to grow the crystal. At this time, the process of adding the allulose seed, and after producing a small amount of crystal nucleus by slowly stirring at the temperature of 35° C., growing the crystal by decreasing the temperature by 1° C. per hour, and dissolving the microcrystal by increasing the temperature of solution to the range of 30 to 35° C. for redissolving the microcrystal produced in the cooling of the crystal growing process. The crystal growing process and microcrystal dissolving process were repeated at least one or more times to perform the crystallization. The allulose crystal produced herein was recovered by drying after removing the mother liquor by centrifuged dehydration and washing the crystal obtained by the primary crystallization with cooling water.

The content of allulose and content of allulose conversion material (Impurity-S) of raw material for crystallization, and the purity of allulose crystal were analyzed under the following analysis conditions.

Analysis column: Biolad Aminex HPX-87C column
Mobile phase: water
Flow rate: 0.6 ml/min
Column temperature: 80° C.
Detector: RI detector As the result of HLPC analysis, the content of allulose conversion material (Impurity S) in aqueous allulose solution for crystallization was 0.4 wt/wt %, and the content of allulose was 97.0 wt/wt %.

The yield of allulose crystal prepared by the method was 63.6%. The yield was represented as a percentage of the weight of recovered allulose crystal powder to the weight of solid of raw material allulose syrup for crystallization.

Examples 2 and 3: Allulose Crystal Preparation

By performing the substantially same method as the allulose preparation of Example 1, the high-purity syrup of allulose comprising 96.6 wt/wt % of allulose was obtained at the concentration of 35 Bx (w/w %) in Example 2, the high-purity syrup of allulose comprising 95.8 wt/wt % of allulose was concentrated to obtain 35 Bx (w/w %) of syrup in Example 3, and the high-purity syrup of allulose comprising 95.5 wt/wt % of allulose was concentrated to obtain 35 Bx (w/w %) of syrup in Example 6. By concentrating the allulose solutions, Example 2 prepared the allulose syrup of 81 Bx (w/w %) for crystallization including 96.6 wt/wt % allulose with 81 Bx (w/w %) and the conductivity of 14 uS/cm, Example 3 prepared the allulose syrup of 81 Bx (w/w %) for crystallization including 95.8 wt/wt % allulose with 81 Bx (w/w %) and the conductivity of 14 uS/cm, and in Example 6, the allulose syrup for crystallization including 95.5 wt/wt % allulose with 81 Bx (w/w %) and the conductivity of 12 uS/cm was prepared. The conductivities of the allulose syrup were values measured on a solid content basis of 30 Bx.

According to the same crystallization method as Example 1, the concentrated allulose syrup was crystallized and the crystals were washed with cooling water, and dried to recover the crystals.

According to the same method as Example 1, The content of allulose and content of allulose conversion material (Impurity-S) of raw material for crystallization, and the purity of allulose crystal were analyzed and the result was shown in the following Table 1.

Specifically, the yield of the allulose crystals prepared from the allulose syrup for crystallization in Example 2 (the content of the allulose conversion material of 0.3 wt/wt %, and the content of the allulose of 96.6 wt/wt %) was 61.9%, the yield of the allulose crystals prepared from the allulose syrup for crystallization in Example 3 (the content of the allulose conversion material of 0.5 wt/wt %, and the content of the allulose of 95.8 wt/wt %) was 61.6%, and the yield of the allulose crystals prepared from the allulose syrup for crystallization in Example 6 (the content of the allulose conversion material of 0.25 wt/wt %, and the content of the allulose of 95.5 wt/wt %) was 62.1%.

Example 4: Allulose Crystal Preparation

The high purity allulose syrup including 97.0 wt/wt % allulose was obtained at the concentration of 35 Bx (w/w %) by the high purity separation process (SMB) by conducting the substantially same method as the allulose preparation of Example 1.

To minimize the impurities contained in the allulose syrup, it was treated by using the appropriate activated carbon at the temperature of 40° C. for 30 min, and then filtered. The allulose syrup after treating the activated carbon was concentrated to be 81 Bx (w/w %), thereby preparing the allulose syrup for crystallization including 97.3 wt/wt % of allulose with 81 Bx (w/w %) and the conductivity of 10 uS/cm.

The concentrated allulose syrup was cooled slowly from the temperature of 35° C. at the supersaturated state to the temperature of 10° C., to grow the crystal. Then, the process of adding the allulose seed, and after producing a small amount of crystal nucleus by slowly stirring at the temperature of 35° C., growing the crystal by decreasing the temperature by 1° C. per hour, and dissolving the microcrystal by increasing the temperature of solution to the ranges of 30~35° C. to redissolve the microcrystal produced in the cooling in the crystal growing process was carried out. The crystal growing process and microcrystal dissolving process were repeated at least one or more times to perform the crystallization. The allulose crystal produced herein was recovered by drying after removing the mother liquor by centrifuged dehydration and washing the crystal obtained by the primary crystallization with cooling water.

Example 5: Allulose Crystal Preparation

The high purity allulose syrup including 97.0 wt/wt % allulose was concentrated to obtain the concentration of 35 Bx (w/w %) by the high purity separation process (SMB) by conducting the substantially same method as the allulose preparation of Example 1.

The allulose syrup was concentrated and the high purity allulose syrup including 97 wt/wt % allulose based on the solid content of 100 wt/wt % was concentrated at the concentration of 81 Bx (w/w %), thereby preparing the allulose syrup for crystallization having the conductivity of 8 uS/cm. According to the same crystallization method as Example 1, the concentrated allulose syrup was crystallized and the crystals were washed with cooling water, and dried to recover the crystals.

The obtained primary crystal was dissolved in water, thereby preparing the allulose dissolved solution of 81.2 Bx, and as the result of analyzing the allulose dissolved solution by the HPLC analysis of Example 1, the content of allulose conversion material (Impurity S) was 0.07 wt/wt % and the content of allulose was 99.5 wt/wt %.

The secondary crystallization process was performed with the prepared allulose dissolved solution as a raw material of secondary crystallization process by substantially same method as the primary crystallization method. The secondary crystal prepared herein was recovered by drying after removing the mother liquor by centrifuged dehydration and washing the crystal obtained by the secondary crystallization with cooling water. The yield of secondary crystal was 62.5%.

TABLE 1

| Classification | Content of allulose of crystallization undiluted solution (%) | Content of Impurity-S of crystallization undiluted solution (%) | Crystallization yield (%) |
| --- | --- | --- | --- |
| Example 1 | 97.0 | 0.4 | 63.6 |
| Example 2 | 96.6 | 0.3 | 61.9 |
| Example 3 | 95.8 | 0.5 | 61.6 |
| Example 4 | 97.3 | 0.2 | 62.0 |
| Example 5 | 99.5 | 0.07 | 62.5 |
| Example 6 | 95.5 | 0.25 | 62.1 |

As shown in the Table 1, it was confirmed that the allulose crystallization yields of Examples 1 to 3 were over 60%, on the other hand, Comparative Example 1 could not obtain proper crystal when the content of allulose conversion material (Impurity-S) was more than 2 wt/wt %, although the allulose content of crystallization undiluted solution was high, and the crystallization yield was drastically decreased due to small crystals.

Comparative Example 1: Allulose Crystal Preparation when the Content of the Allulose Conversion Material Exceeds 2 wt/wt %

In order to determine the yield of the allulose crystals when the content of the allulose conversion material in the crystallization solution was more than 2 wt/wt %, acidic pH condition or heat treatment condition was applied to the crystallization solution for secondary crystallization in Example 5 to trigger the formation of the allulose conversion material.

Specifically, the starting material for secondary crystallization was prepared by dissolving the allulose crystal obtained by performing the primary crystallization in Example 5 in water, and then be heat-treated at the conditions of pH 3.5 and the temperature of 80° C. for 3 hours. According to the same crystallization method as Example 1, the concentrated allulose syrup was crystallized and the crystals were washed with cooling water, and dried to recover the crystals.

According to the same method as Example 1, the content of allulose and content of allulose conversion material (Impurity-S) of raw material for crystallization, and the purity of allulose crystal were analyzed and the result was shown in the following Table 2.

Comparative Examples 2 and Example 7 to 8: Allulose Crystal Preparation Method by the Content of Allulose Conversion Material The starting material for secondary crystallization was prepared by dissolving the allulose crystal obtained by performing the primary crystallization in Example 5 in water, and then be treated at the conditions of pH 4.5 and the temperature of 70° C. for 6, 13 or 24 hours. The content of allulose and content of allulose conversion material (Impurity-S) of raw material for crystallization were shown in Table 2.

The method of proceeding crystallization using the prepared crystallization solution was carried out in substantially the same method as in Example 1. Specifically, in Comparative Example 2 and Examples 7 to 8, the allulose crystallization processes were performed using different allulose crystallization solution with different heat treatment time, having different allulose content and the allulose conversion material shown in Table 2.

According to the same method as Example 1, the content of allulose and content of allulose conversion material (Impurity-S) of raw material for crystallization, and the purity of allulose crystal were analyzed and the result was shown in the following Table 2.

TABLE 2

| Classification | Content of allulose of crystallization undiluted solution (%) | Content of Impurity-S of crystallization undiluted solution (%) | Crystallization yield (%) |
|---|---|---|---|
| Comparative Example 1 | 97.0 | 2.1 | 42.4 |
| Example 7 | 98.5 | 0.65 | 58.8 |
| Example 8 | 96.2 | 1.50 | 53.1 |
| Comparative Example 2 | 93.3 | 3.40 | 29.1 |

In case of Comparative Example 2, since the purity of allulose was low and the content of allulose conversion material was high, the growth of crystal particles was not gone well and microcrystals were produced, and thus dehydration and washing of crystals were very difficult. In case of Comparative Example 1, it was confirmed that the growth of crystal particle size was not gone well and microcrystals were produced as the content of allulose conversion material was higher, as same as Comparative Examples 2. In case of Example 7 and Example 8, it was confirmed that the content of the allulose conversion material was lower than 2 wt/wt %, indicating a high crystal yield compared to that of the comparative example.

Experimental Example 1

LC-MS Analysis of Allulose Conversion Material (Impurity S)

(1) Analysis of Allulose Conversion Material (Impurity S) of Example 2

The impurities fraction isolated in the peak at the elution time 31±2 min was directly collected in HPLC analysis of allulose syrup for crystallization used in Example 2, and the solution diluted during the separation fraction was freeze-dried and concentrated at approximately 100 times concentration used for the analysis. The molecular weight of allulose conversion material (Impurity S) measured by LC/MS analysis by conducting the analysis of molecular weight of impurities with the liquid chromatograph/mass analyzer (LC/MS system, model name: LTQ, manufacturer: Thermo Finnigan, USA) was the material having the range of 300 to 400 m/z (ratio of mass/quantity of electric charge).

(2) Analysis of Allulose Conversion Material (Impurity S) of Comparative Examples 2 and Examples 7 to 8

According to the substantially same as the LC-MS analysis method, the thermal treated crystallization undiluted solutions used in Comparative Examples 2 and Examples 7 to 8 was used. For the changes of molecular weight of allulose and allulose conversion material according to the thermal treatment, LC-MS analysis was conducted, and the result of analysis of content of allulose and content of allulose conversion material (%) comprised in the crystallization undiluted solutions used in Comparative Examples 2 and Examples 7 to 8 was shown in the following Table 3.

The following Table 3 is data of LC-MS analysis of allulose syrup by thermal treatment time (Example 7, Example 8, Comparative Examples 2), and the numerical values, which the values of area of peak detected by each molecular weight (m/z) were converted into a percentage, were shown in the table. The molecular weight of 179.1 m/z in Row 1 of Table 3 was allulose. Rows 4, 8 and 10 in the following Table 3 represented that the content of allulose conversion material (Impurity S) was increased after the thermal treatment, and the other Rows represented that the content of allulose conversion material (Impurity S) was decreased after the thermal treatment.

TABLE 3

| Row | m/z | Example 5 | Example 7 | Example 8 | Comparative Example 2 | Formula Finder Result |
|---|---|---|---|---|---|---|
| 1 | 179.1 | 56.68 | 38.53 | 31.65 | 24.75 | C6H12O6 |
| 2 | 225.1 | 9.27 | 6.26 | 5.12 | 4.26 | C7H14O8 |
| 3 | 251.1 | 0.36 | 1.05 | 1.09 | 1.18 | C9H16O8 |
| 4 | 341.1 | 6.03 | 16.68 | 18.99 | 19.71 | C12H22O11 |
| 5 | 359.1 | 21.31 | 14.66 | 11.50 | 8.42 | C12H24O12 |
| 6 | 387.1 | 1.37 | 3.44 | 3.91 | 4.76 | C13H24O13 |
| 7 | 485.1 | 0.04 | 0.06 | 0.17 | 0.61 | C18H30O15 |

TABLE 3-continued

| Row | m/z | Example 5 | Example 7 | Example 8 | Comparative Example 2 | Formula Finder Result |
|---|---|---|---|---|---|---|
| 8 | 503.2 | 0.44 | 2.11 | 5.53 | 9.89 | C25H28O11 |
| 9 | 665.2 | 0.06 | 0.16 | 0.60 | 2.03 | C24H42O21 |
| 10 | 683.2 | 4.13 | 16.01 | 18.50 | 18.51 | C24H44O22 |
| 11 | 711.2 | 0.02 | 0.02 | 0.15 | 0.56 | C25H44O23 |
| 12 | 827.3 | 0.01 | 0.02 | 0.06 | 0.35 | C37H48O21 |
| 13 | 845.3 | 0.09 | 0.60 | 1.37 | 1.92 | C30H54O27 |
| 14 | 1007.3 | 0.01 | 0.13 | 0.90 | 2.31 | C36H64O32 |

As shown in the analysis result, it was confirmed that the content of allulose was lowered and the content of impurities was raised in the molecular weight analysis as the thermal treatment time was increased. The molecular weight of 179.1 m/z in Row 1 of the Table 3 was allulose, and it was confirmed that the numerical value of peak area value was decreased after the thermal treatment. On the other hand, it could be confirmed that the component detected in the molecular weight of 341 m/z (Table Row 5) was the component increased as thermal treating the crystallization undiluted solution containing allulose, and the material of Dimer-like structure that allulose was modified by dehydration or condensation reaction. As the result of inferring the structure by LC-MS analysis, it could be predicted that it was the material having the chemical formula of C12H22O11, and the allulose denatured polymer. It was confirmed that the content of allulose denatured polymers (tetramer analogues of allulose) having the molecular weight similar to dimer of allulose denatured polymer of C25H28O11, C24H42O21 or C24H44O22 as the thermal treatment was proceeded additionally. This could be considered that the allulose was easily denatured by external stress, for example, acidic pH and/or thermal treatment in Comparative Examples 1 or 2 and the dehydration and condensation reactions were randomly repeated with allulose or allulose conversion material, thereby being converted into the above materials.

(3) Analysis of the Allulose Conversion Material of Example 3

In the HPLC analysis of the allulose syrup for crystallization used in Example 3, the separated impurity fraction was directly obtained at a peak of the elution time of 31+/−2 minutes, and the fraction diluted during the HPLC analysis was lyophilized and concentrated about 100 times, and used for analysis.

Name of analyzer: Ultimate-3000 ISQ EC (Thermo Fisher)
Analytical column: Bio-rad Aminex HPX-87C
Column temperature: 80° C.
Flow rate: 0.3 mL/min
Solvent: distilled water
Injection volume: 5 μℓ

As a result of LC/MS analysis of the allulose conversion material, there were peaks near at 55.22 m/z, 60.24 m/z, 74.14 m/z, 79.25 m/z, 82.22 m/z, 83.23 m/z, 109 m/z, 117 m/z, 124.26 m/z, 127.1 m/z, 141.5 m/z, 144 m/z, 163.23 m/z, 203.16 m/z, and 365.16 m/z, and the main peaks were near at 127 m/z, 163 m/z, 198.2 to 203 m/z, and 365 m/z.

Therefore, the allulose conversion material is a derivative material from allulose which is a molecule composed of C, H, and O having 5 to 12 carbon atoms (C), has a molecular weight charge value of 50 m/z or more to 400 m/z or less, contains HMF and levulinic acid components, and includes a derivative material containing a furan structure. Specifically, in the case of the 163 m/z peak, it is considered that an intermediate substance (Furan aldehyde intermediate) from the process in which hexose such as allulose is decomposes to HMF by dehydration reaction. In the case of a peak of 198.2 to 203 m/z, it is considered to be a $[C_6H_{12}O_6+Na]^+$ molecule in which a $Na^+$ ion is bonded to an allulose molecule, and in the case of 365 m/z peak, it is considered to be $[C_6H_{12}O_6+Na]^+$ molecule in which a $Na^+$ ion is bonded to an allulose dimer molecule.

Based on the LC/MS analysis results of the allulose conversion material, the compounds included in the allulose conversion material are shown in Table 4 below.

TABLE 4

| name | Formula | molecular weight (g/mol) |
|---|---|---|
| levulinic acid(4-oxopentanoic) | C5 H8 O3 | 116.1 |
| furfural | C5 H4 O2 | 96.08 |
| HMF | C6 H6 O3 | 126.1 |
| γ-Hydroxyvaleric acid GVB | C5 H10 O3 | 118.13 |
| 2,5-Dimethylfuran | C6 H8 O | 96.13 |
| 2,5-Furandicarboxylic acid | C6 H4 O5 | 156.09 |
| 5-hydroxymethyl-2-furoic acid | C6 H6 O4 | 142.1 |
| 2,5-formylfurancarboxylic acid | C6 H4 O4 | 140 |
| 2,5-Furandicarbaldehyde | C6 H4 O3 | 124 |
| 2,5-bis-(hydroxymethyl)furan | C6 H8 O3 | 128 |
| bis(5-formyl-2-furfuryl) ether | C12 H10 O5 | 234 |
| 2,5-Furandicarboxylic acid | C6 H4 O5 | 156 |
| 2-Furoic acid | C5 H4 O3 | 112 |
| 5-Hydroxyfurfural | C5 H4 O3 | 112 |
| 3-Furoic acid | C5 H4 O3 | 112 |
| 2,5-Dihydro-2,5-dimethoxyfuran | C6 H10 O3(C6H12O3) | 130 (132) |
| (2R)-5-Oxotetrahydro-2-furancarboxylic acid | C5 H6 O4(C6H8O4) | 130 (132) |
| 2,5-formylfurancarboxylic acid(140) | C6 H4 O4 | 138 |
| 5,5'-Methylenedi(2-furoic acid) (dimer form) | C11 H8 O6 | 236 (234) |
| bis(5-methyl furfuryl) ether (—OH form) | C12 H12 O5 | 236 (234) |

(4) LC/MS Analysis of 5-HMF

LC/MS analysis of 5-HMF was performed to confirm that 5-HMF was included in the allulose conversion material.

As a 5-HMF analysis sample, a standard substance (SIGMA-ALDRICH, CAS Number 67-47-0) was purchased and used.

As a result, the molecular weight m/z values of the structures which can be generated from 5-HMF by charge transfer, elimination and dehydration in aqueous solution state were measured, having the peaks at 79.09 m/z, 109 m/z, 124.22 m/z, 127 m/z, 144.15 m/z etc, which are partially identical to the result of LC/MS analysis result of the allulose conversion material, indicating that 5-HMF was contained in the allulose conversion material.

Experimental Example 2: Allulose Stability Analysis

In order to test the effect by temperature of allulose and allulose conversion material, the allulose syrup including 97 wt/wt % of allulose of Example 1 was divided and placed in the same amount of 30 g each and stored in constant-temperature water baths of different temperatures each other, and sampled by time, thereby analyzing the content changes, and the result was shown in FIG. 1 and FIG. 2.

FIG. 1 is the graph showing the content changes of allulose, when the 70% Brix concentration of allulose syrup of pH 5 was stored by temperature. FIG. 2 is the graph showing the content changes of allulose conversion material, when the 70% Brix concentration of allulose syrup of pH 5 was stored by temperature. As shown in FIG. 1 and FIG. 2, as the storage temperature was higher, the content of allulose was decreased and the content of allulose conversion material (Impurity-S) was increased.

In addition, to test the effect according to pH of allulose and allulose conversion material, after controlling the syrup of 97.0% allulose content of Example 1 at respectively different pH by using caustic soda and hydrochloric acid solution, it was stored at the same temperature (70° C.) and sampled by time, thereby analyzing the content changes, and the result was shown in FIG. 3 and FIG. 4.

FIG. 3 is the graph showing the content changes of allulose, when the 70% Brix concentration of allulose syrup of different pH was stored at the temperature of 70° C. FIG. 4 is the graph showing the content changes of allulose conversion material, when the 70% Brix concentration of allulose syrup of different pH was stored at the temperature of 70° C. As shown in FIG. 3 and FIG. 4, as the pH was lower at the temperature of 70° C., the content of allulose was decreased and the content of allulose conversion material (Impurity-S) was increased.

Accordingly, since the allulose was unstable as pH was lower and temperature was higher, the content of allulose was changed in the actual production process, particularly concentration step. This problem lowered the purity of high purity of allulose, and therefore, largely affected the crystallization step. It was confirmed that the content of specific allulose conversion material (Impurity) produced additionally as the content of allulose was decreased in this process actually, and this component largely affected the crystallization of allulose. It was confirmed that when the content of component of Impurity-S in the various allulose conversion materials was over 2%, this might act as major barrier factor for the growth of allulose crystal particle, and thereby largely affect the particle size of crystal particle and crystallization yield.

Example 3: Analysis of Allulose Crystal Characteristics (1): Analysis of Crystal Particle Size Distribution The particle size distribution of allulose crystal obtained in Example 5 was confirmed by using standard sieves by Mesh. The Mesh sizes of standard sieves were 20, 30, 40, 60, 80, 100 mesh, and the size distribution of crystal particle was measured by the hole-sizes of standard sieves.

The hole-sizes of standard sieves by each mesh were 850, 600, 425, 250, 180, and 150 μm. 100 g of each sample was collected and put in standard sieves by mesh size, and passed through the standard sieves by adding vibration. The percentage values were described in Table 5 by measuring the weight of samples remained in sieves by each mesh size. In the following Table 5, the particle size distribution by each mesh was represented by wt % of particle with numerical values.

TABLE 5

| Mesh size (mesh) | 100 mesh pass | 100mesh↑ | 80mesh↑ | 60 mesh↑ | 40 mesh↑ | 30 mesh↑ | 20 mesh↑ |
|---|---|---|---|---|---|---|---|
| Particle size(μm) | =150 | 150< | 180< | 250< | 425< | 600< | 850< |
| Example 5 | 0.9 | 2.6 | 5.9 | 20.2 | 70.0 | 0.4 | 0 |

As shown in the Table 5, it was confirmed that the allulose crystal of Example 5 exhibited very narrow distribution converging into 90.2 wt % of the particle distribution, and the allulose crystal of Example 3 exhibited the most distribution in 40↑, but the particle distribution was widely spread as evenly distributed in 80↑, 60↑, 40↑, and 30↑. It was confirmed that the hard crystal particle having low ratio of long diameter/short diameter as Example 5 had relatively low content of micronized products and uniform distribution of particle size. In addition, the particle having high ratio of long diameter/short diameter and low homogeneity may be micronized by particle breakage in the drying and transferring processes and the particle size may be heterogeneous, thereby having the wide range of particle size distribution.

(2) Analysis of Crystal Form and Crystal Particle Size

Figure 5:
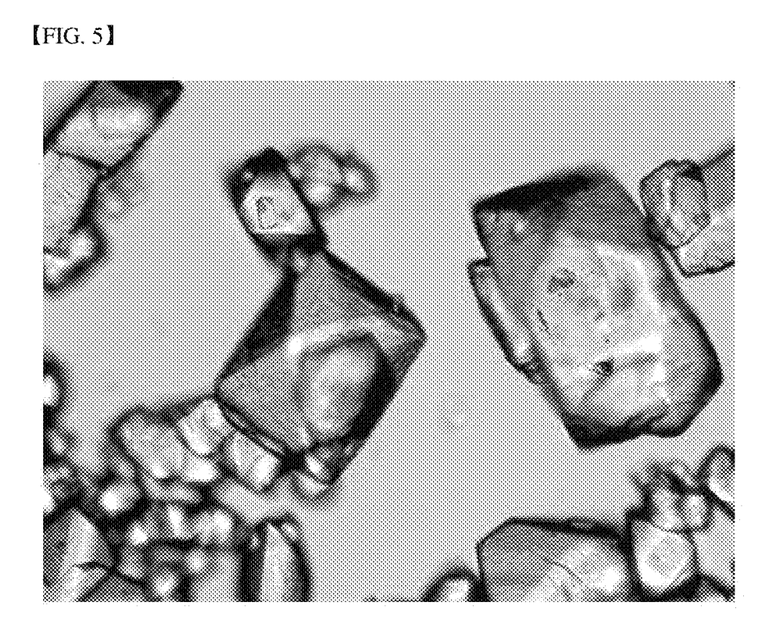
FIG. 5 is an optical microscopic photograph of allulose powder obtained in Example 5 measured at magnification ×100.

The optical microscopic photographs of allulose crystals obtained in Example 5 measured by magnification X100 were shown in FIG. 5. The scanning microscopic photograph (SEM) of allulose crystals obtained in Example 5 measured by magnification ×100 were shown in FIG. 6.

In addition, the long diameters (height) and short diameters (width) for 9 samples of allulose crystals obtained in Example 5 were measured, and the particle diameter ratio (=long diameter/short diameter) was obtained and shown in the following Table 6. Specifically, for 5 crystals, the ratio of length of long diameter (μm) was shown, on the basis of short diameter length (μm) as 1.

TABLE 6

| Crystals | Example 5 |
|---|---|
| #1 | 1.3 |
| #2 | 1.5 |
| #3 | 1.2 |
| #4 | 1.2 |
| #5 | 2.1 |
| #6 | 1.7 |
| #7 | 1.7 |
| #8 | 1.4 |
| #9 | 2.4 |
| average | 1.6 |

Figure 6:
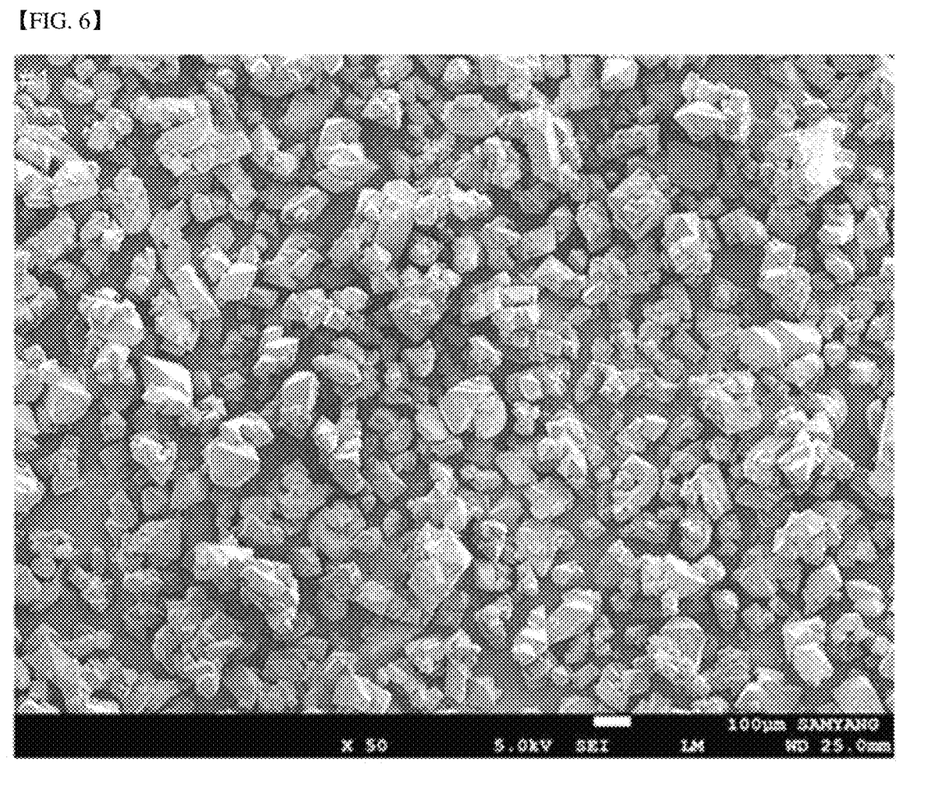
FIG. 6 is a scanning electron microscope (SEM) photograph of allulose powder obtained in Example 5 measured at magnification ×50.

As shown in FIG. 6, the allulose crystal of the present invention had a rectangle hexahedron or crystal structure close thereto. The ratio of long diameter length (μm) to the short diameter length (μm) of 1 of crystals in the Table 5 showed that average 1.6 in Example 5. Example 5 formed the crystal form of rhombic system close to quadrate as each crystal side was grown homogeneously. In addition, it was confirmed that the ratio of long diameter/short diameter tended to be reduced, as the crystal side was grown homogenously. This was suggested that since other components except for allulose acted as impurities disrupting the crystal growth of pure allulose, as the allulose purity in raw material for crystallization was low, they affected the crystal shape.

(3) Differential Scanning Calorimetry (DSC) Analysis

The DSC analysis of allulose crystals obtained in Example 5 was performed under the specific DSC analysis conditions.

Equipment name DSC [differential scanning calorimetry]
Manufacturer: Perkin Elmer
Method: 30 to 250° C., 10° C./min temperature rising, N2 gas purge
(standard method: refer to ASTM D 3418)

The result of DSC analysis of allulose crystal was shown in the following Table 7.

TABLE 7

| Classification | Tm(° C.) | ΔH(J/g) |
|---|---|---|
| Example 5 | 127.89 | 207.5 |

As the result of DSC analysis, the crystal in Example 5 had the highest Tm value, and the highest thermal capacity. It could be predicted that as the thermal capacity was higher in the DSC analysis of crystal, it was not easily dissolved, and as the thermal capacity was higher and the width of endothermic peak was narrower, the crystal was formed homogeneously and firmly. In consideration of thermal capacity and endothermic peak enthalpy values of Example 5, it was confirmed that the crystal of Example 5 was formed relatively more homogeneously and firmly.

(4) Infrared Absorption (IR) Spectrum Analysis

To confirm the prepared allulose crystal, the infrared absorption (IR) spectrum analysis was carried out for the crystals of Example 5, under the measuring conditions.

Analysis equipment: TENSOR II with Platinum ATR, manufacturer; Bruker (German)
Detector: highly sensitive photovoltaic MCT detector with liquid nitrogen cooling.
Scan number of times: 64 scans at 20 kHz
Scan range: 800-4,000 $cm^{-1}$ and averaged at 4 cm-1 resolution.

According to the result of infrared absorption (IR) spectrum analysis for the allulose crystal according to the present invention, the allulose crystal had unique structural characteristic as the allulose molecule included functional groups —OH, and C—O—C, C—C, C—OH, etc. in the allulose molecular structure. It demonstrated that the crystals of Example 5 were identical allulose crystals.

(5) X-Ray Diffraction (XRD) Analysis

The X-ray diffraction analysis was performed according to the following specific analysis conditions, for the allulose crystals obtained in Example 5, and the result of X-ray diffraction analysis of allulose crystals obtained in Example 5 was shown in Table 8 by selecting the higher (Relative Intensity %) five peaks and morphology specific peaks.

Analysis equipment: D/MAX-2200 Ultima/PC
Manufacturer: Rigaku International Corporation (Japan)
X-ray sauce system target: sealed tube Cu
Tube voltage: 45 kV/Tube current: 200 mA
Scan range: 5 to 80° 2θ
Step size: 0.019°
Scan speed: 5°/min

TABLE 8

| Angle 2-Theta degree | Relative Intensity % |
|---|---|
| 18.78 | 100.0 |
| 15.24 | 97.6 |
| 28.37 | 9.5 |
| 30.84 | 18.8 |
| 31.87 | 9.0 |
| 47.06 | 4.1 |

As shown in the Table 8, it was confirmed that the allulose crystal obtained in Example 5 had specific peaks in 15.24, 18.78 and 30.84; 15.24, 18.78, 30.84, and 28.37; 15.24, 18.78, 30.84 and 31.87; 15.24, 18.78, 30.84 and 47.06; or 15.24, 18.78, 30.84, 28.37, 31.87 and 47.06; of 2θ values in the powder X-ray spectroscopy.

The invention claimed is:

1. A method for controlling the content of allulose conversion material (Impurity-S) contained in a composition for crystallizing allulose as 2 wt/wt % or lower, based on the solid content, comprising
adjusting pH condition of an allulose solution in a range of 4.5 to 7;
concentrating the allulose solution to obtain the composition for crystallizing allulose, and
cooling the composition for crystallizing allulose to prepare allulose crystal,
wherein the allulose conversion material contains a compound of molecular formula $C_xH_yO_z$,
wherein
x is an integer from 3 to 15,
y is an integer from 1 to 15, and
z is an integer of 1 to 10.

2. The method of claim 1, wherein the step of concentrating is performed at a temperature of 40° C. to 70° C.

3. The method of claim 1, wherein the allulose conversion material contains one or more kinds selected from the group consisting of
allulose dimer,
allulose tetramer,
levulinic acid (4-oxopentanoic),
furfural,
Hydroxymethylfurfural (HMF),
γ-Hydroxyvaleric acid (GVB),
2,5-Dimethylfuran,
2,5-furandicarboxylic acid (FDCA),
5-hydroxymethyl-2-furoic acid,
2,5-formylfurancarboxylic acid,
2,5-Furandicarbaldehyde,
2,5-bis-(hydroxymethyl)furan,
bis(5-formyl-2-furfuryl) ether,
2-Furoic acid,
3-Furoic acid,
5-Hydroxyfurfural,
2,5-Dihydro-2,5-dimethoxyfuran,
(2R)-5-Oxotetrahydro-2-furancarboxylic acid,
2,5-formylfuran carboxylic acid,
5,5'-Methylenedi(2-furoic acid), and
bis(5-methyl furfuryl) ether.

4. The method of claim 1, further comprising treating a reaction solution containing allulose with an SMB chromatography separation process to obtain the allulose solution.

5. The method of claim 4, wherein the concentration process is performed as divided into at least two stages, wherein a primary concentration for the allulose solution is performed to be 30 to 50 Bx to obtain a primary concentrate and the primary concentrate is secondarily concentrated to be 60 to 85 Bx.

6. The method of claim 4, further comprising treating an activated carbon, before conducting the concentration process.

7. The method of claim 1, wherein the composition for crystallizing allulose is provided as a dissolved solution in which an allulose crystal or powder is dissolved in water.

8. The method of claim 1, wherein the composition for crystallizing allulose has the conductivity of 1,000 uS/cm or lower.

9. The method of claim 1, wherein the allulose conversion material contains 10 to 600 m/z of the ratio of mass/quantity of electric charge measured by an LC/MS analysis method.

10. The method of claim 1, wherein the allulose conversion material contains material having a maximum peak at elution time of 31 min ±2 min time measured by a HPLC analysis method.

* * * * *